US008986219B2

(12) United States Patent
Layton

(10) Patent No.: US 8,986,219 B2
(45) Date of Patent: Mar. 24, 2015

(54) LUMEN OCCLUSION DETECTION

(71) Applicant: Hologic, Inc., Marlborough, MA (US)

(72) Inventor: Russell Layton, Acton, MA (US)

(73) Assignee: Hologic, Inc., Marlborough, MA (US)

( * ) Notice: Subject to any disclaimer, the term of this patent is extended or adjusted under 35 U.S.C. 154(b) by 6 days.

(21) Appl. No.: 14/034,913

(22) Filed: Sep. 24, 2013

(65) Prior Publication Data

US 2014/0024965 A1    Jan. 23, 2014

Related U.S. Application Data

(63) Continuation of application No. 12/950,901, filed on Nov. 19, 2010, now abandoned.

(51) Int. Cl.
| *A61B 5/00* | (2006.01) |
| *A61B 5/103* | (2006.01) |
| *A61B 5/117* | (2006.01) |
| *A61B 5/03* | (2006.01) |
| *A61M 13/00* | (2006.01) |

(52) U.S. Cl.
CPC .............. *A61B 5/4325* (2013.01); *A61B 5/035* (2013.01); *A61M 13/003* (2013.01); *A61M 2205/3334* (2013.01)
USPC .......................................... 600/561; 600/591

(58) Field of Classification Search
CPC .......... A61B 5/036; A61B 17/42; A61B 5/03; A61B 5/003; A61B 5/035; A61M 25/10; A61M 2025/1052; A61M 2025/1072; A61M 2205/3331

USPC ..................... 600/185, 486, 561, 591; 73/700
See application file for complete search history.

(56) References Cited

U.S. PATENT DOCUMENTS

| 4,700,694 | A | 10/1987 | Shishido |
| 7,220,259 | B2 | 5/2007 | Harrington et al. |
| 2004/0068226 | A1 | 4/2004 | Brannon |
| 2004/0127813 | A1* | 7/2004 | Schwamm ..................... 600/561 |
| 2005/0240211 | A1 | 10/2005 | Sporri et al. |
| 2005/0283092 | A1 | 12/2005 | Gedebou |
| 2007/0123781 | A1 | 5/2007 | Callahan et al. |
| 2008/0167664 | A1 | 7/2008 | Payne et al. |
| 2009/0062611 | A1 | 3/2009 | Toyama |
| 2009/0137968 | A1 | 5/2009 | Rottenberg |
| 2009/0182319 | A1* | 7/2009 | Lane et al. ...................... 606/21 |
| 2009/0209951 | A1 | 8/2009 | Marrouche |
| 2009/0326526 | A1* | 12/2009 | Ingle et al. ...................... 606/21 |
| 2010/0198214 | A1 | 8/2010 | Layton, Jr. et al. |
| 2010/0234855 | A1* | 9/2010 | Wahr et al. .................... 606/127 |
| 2011/0087109 | A1* | 4/2011 | Swann .......................... 600/476 |

* cited by examiner

*Primary Examiner* — Max Hindenburg
*Assistant Examiner* — Jonathan M Foreman
(74) *Attorney, Agent, or Firm* — Vista IP Law Group LLP

(57) ABSTRACT

Devices and methods are disclosed to detect or verify fallopian tube occlusion. Devices include an elongated body, a continuous open space extending between proximal and distal openings, a first pressure sensor or flow meter configured to measure a pressure or fluid flow within the continuous open space, at least one seal member protruding from the outer wall of the elongated body, and a second pressure sensor or flow meter configured to measure a pressure or flow meter within a space created by the at least one seal member.

16 Claims, 4 Drawing Sheets

LUMEN OCCLUSION DETECTION

RELATED APPLICATION DATA

This application is a continuation application of co-pending U.S. patent application Ser. No. 12/950,901, filed Nov. 19, 2010, the priority of which is claimed under 35 U.S.C. §120, and the contents of which are incorporated herein by reference in their entirety, as though set forth in full.

FIELD OF THE INVENTION

The present invention generally relates to devices and methods used to verify or detect occlusion of a body lumen, such as a fallopian tube.

BACKGROUND

Current female sterilization procedures often make use of implants that are placed within the fallopian tubes. For example, the Adiana® Permanent Contraception (Hologic, Inc., Marlborough, Mass.) is a minimally invasive procedure in which a delivery catheter is passed through the vagina and cervix and into the uterus. A low level of radiofrequency energy is delivered to a small section of each fallopian tube to create a superficial lesion. A small implant is then placed within each fallopian tube at the location where the lesions were created. Over a period of time, tissue grows into and/or around the implants leading to complete occlusion of the fallopian tubes to thereby provide the desired sterilization. Such implants and procedures are described, for example, in U.S. Pat. No. 7,220,259, which is incorporated herein by reference.

It is often desired, and clinically required per the FDA approved instructions for use (IFU) of the product, to use a post-procedure verification method to ensure that the fallopian tube(s) have indeed been fully occluded to yield the desired sterilization. Typically, occlusion is verified after the sterilization procedure with the aid of hysterosalpingogram (HSG). An HSG is a radiographic technique in which a contrast media (e.g., oil or water soluble fluid containing a radiographically opaque compound of a material such as iodine) is injected into the uterine cavity and fallopian tubes via a transcervicallly-placed cannula. Radiographic images are taken to delineate the inside of the uterus and fallopian tubes. Tubal occlusion is verified by the lack of contrast media past a specific location in the tube (or by lack of contrast media in certain anatomical spaces such as the pouch of Douglas). There are several possible limitations to using HSG to verify occlusion. First, the patient and physician are exposed to radiation. Second, the determination of occlusion/patency is done visually and can thus be prone to human error. Tissue and bone of different densities can obstruct the view of pooling contrast media and premature reading of x-rays may not identify slow pooling contrast media. Lastly, a radiologist is needed in addition to a gynecologist, thus complicating this medical procedure and increasing the likelihood for patient non-compliance.

There have been some successful efforts to develop new devices and procedures to verify tubal occlusion following the aforementioned sterilization procedure and similar procedures. For example, US patent publication no. 2008/0167664, which is incorporated herein by reference, describes a device for verifying occlusion of the fallopian tube including an elongate gas delivery having a lumen disposed therein adapted for sealing engagement with the uterus. The device includes a pressurized insufflation gas source coupled to the elongate gas delivery member. The device includes a pressure sensor or gauge to measure intra-uterine pressure to verify occlusion of the fallopian tubes. A possible limitation of this device is that it does not include the ability to confirm a proper seal between the patient's anatomy and the device.

It is an object of the present invention to provide devices and methods to verify or detect occlusion of a body lumen, such as a fallopian tube, that avoid the limitations of the prior art.

SUMMARY OF THE INVENTION

In one aspect, the present invention comprises devices used to verify or detect occlusion of a body lumen, such as a fallopian tube.

In another aspect, the present invention comprises a kit that includes a device used to verify or detect occlusion of a body lumen, such as a fallopian tube.

In yet another aspect, the present invention comprises a method of verifying or detecting occlusion of a body lumen, such as a fallopian tube, using the devices of the present invention.

In certain embodiments, the present invention comprises a device comprising an elongated body comprising a proximal end, a distal end, an outer wall extending between the proximal end and the distal end, a proximal opening, a distal opening, and a continuous open space extending between the proximal and distal openings. The device includes or is in communication with a first pressure sensor and/or flow meter configured to measure a pressure and/or fluid flow within the continuous open space, at least one seal member protruding radially from the outer wall of the elongated body, and a second pressure sensor and/or flow meter configured to measure a pressure and/or fluid flow within a space created by the at least one seal member.

In other embodiments, the present invention comprises a method of detecting or verifying occlusion of a body lumen, such as fallopian tube into which an implant had been placed. The method comprises the steps of providing a device as described above, advancing the distal end of the elongated body into the body lumen and proximal to the implant, creating a seal between the at least one seal member and the patient's tissue, providing a pressurized fluid such as carbon dioxide into the elongated body and thereby into the body lumen, monitoring pressure and/or fluid flow within the elongated body with the first pressure sensor and/or flow meter to detect or verify the effectiveness of the implant, and monitoring pressure and/or fluid flow within the space created by the at least one seal member to detect any leaks of the pressurized fluid from the space created between the implant located in the body lumen and the first seal member.

DESCRIPTION OF THE PREFERRED EMBODIMENTS

The present invention provides devices and methods used to verify or detect occlusion of body lumens, such as fallopian tubes following a sterilization procedure. Although the present invention is described with specific reference to fallopian tubes, it should be recognized that the devices and methods of the present invention are equally applicable to the detection or verification of occlusion within any body lumen, such as a blood vessel, urethra, ureter, or other lumens within the cardiovascular, urogenital, or gastrointestinal systems.

Figure 1:
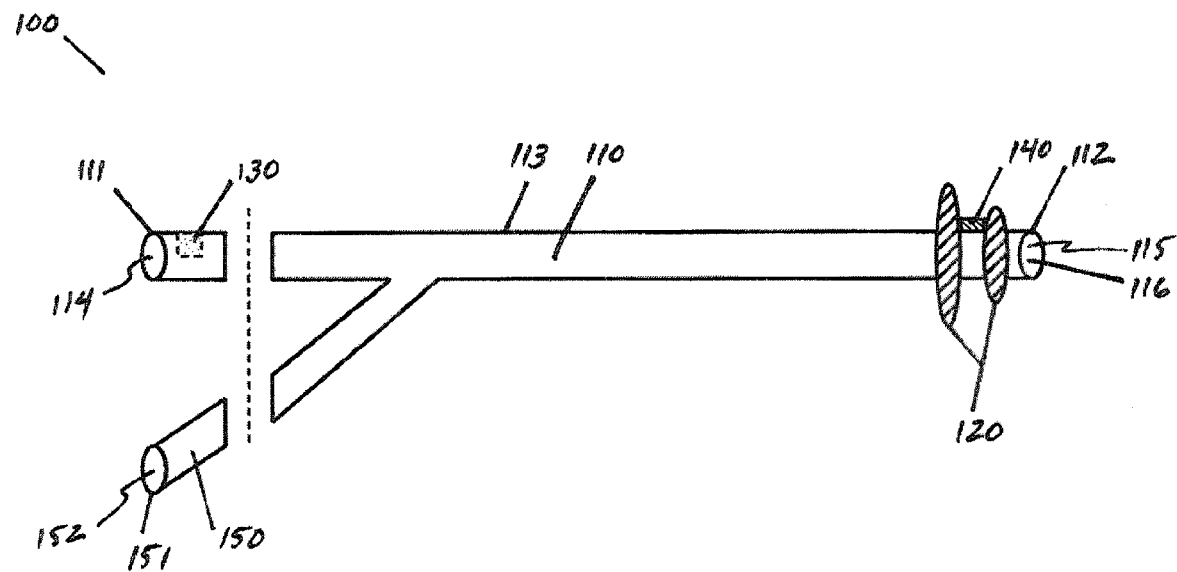
FIG. 1 is a perspective view of device used to detect or verify lumen occlusion, in accordance with an embodiment of the present invention.

An embodiment of a device according to the present invention is shown in FIG. 1. Device 100 comprises an elongated body 110 having a proximal end 111, distal end 112, an outer wall 113 extending between the proximal and distal ends 111, 112, a proximal opening 114, a distal opening 115, and a continuous open space 116 extending between the proximal and distal openings 114, 115. The device further comprises at least one seal member 120, a first pressure sensor and/or flow meter 130, and a second pressure sensor and/or flow meter 140. It should be noted that the pressure sensor and/or flow meter 130 may be located at any suitable location on or near the device 100, so long as it may function properly to measure pressure and/or flow.

Figure 2:
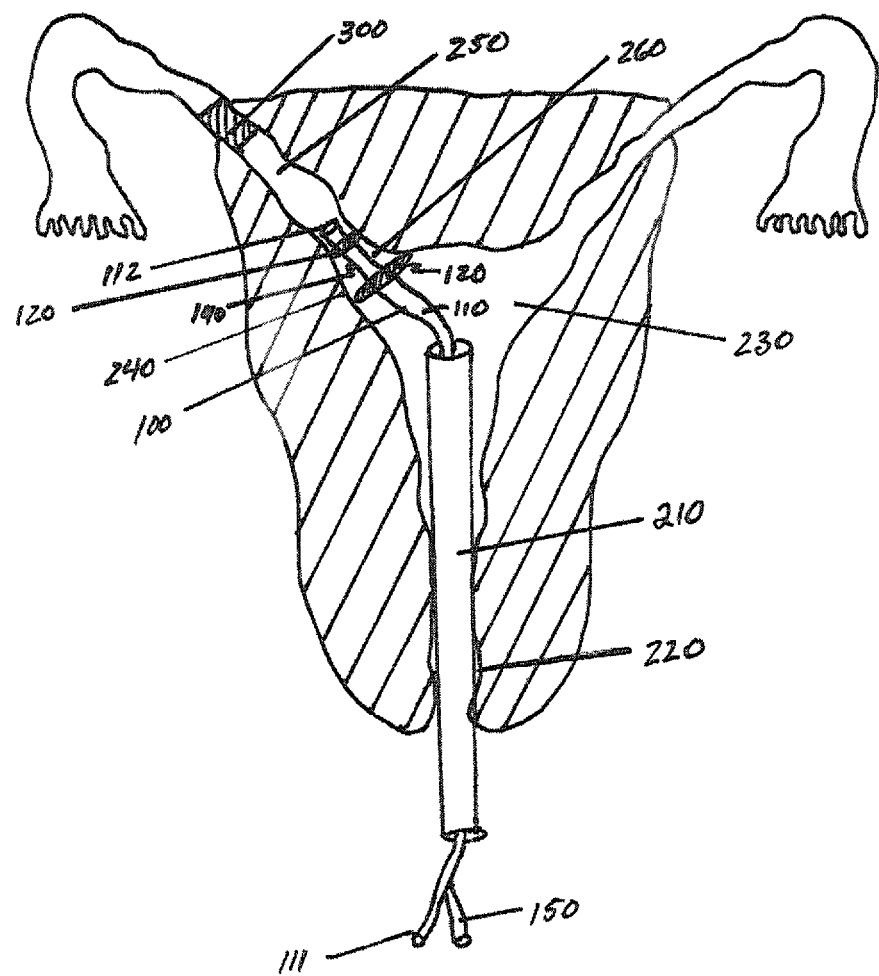
FIG. 2 illustrates the placement of a device of the present invention into the fallopian tube of a patient, in accordance with an embodiment of the present invention.

As shown in FIG. 2, the device of FIG. 1 may be used by inserting an optional cannula 210 into through the vagina 220 and into the uterus 230. The device 100 is advanced through the cannula 210 and distal end 112 is advanced through the uterotubal junction 240 and into the fallopian tube 250 in which an implant 300 has been previously implanted. Preferably, the device is advanced to a position such that the distal end 112 is within a several millimeters of the implant 300. The device 100 is positioned such that the at least one seal member 120 makes sufficient contact with surrounding tissue to create a space 260 that is isolated from the surrounding uterus and/or fallopian tube. Preferably, a light source, viewing scope, and other visualization equipment (not shown) is inserted through cannula 210 and into the uterus to as to help facilitate proper placement of the device 100.

Figure 3:
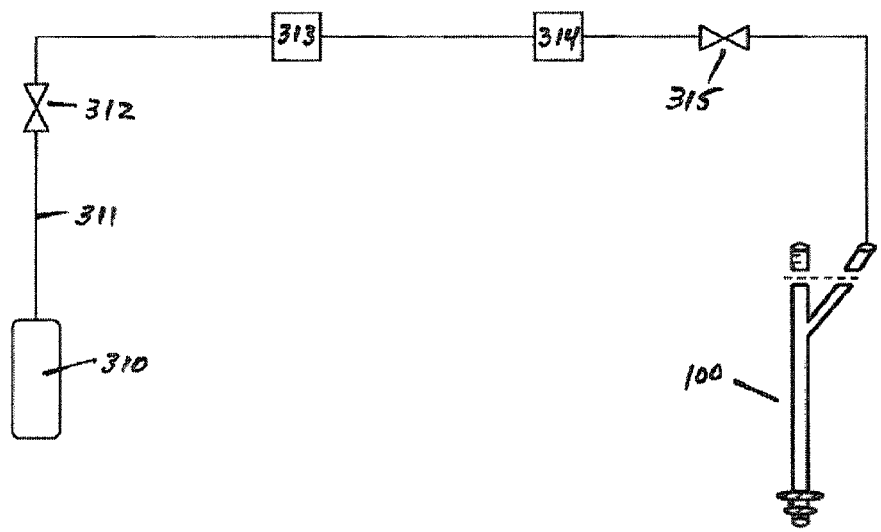
FIG. 3 is a schematic representation of a system used with the device of the present invention.

As shown in the embodiment of FIG. 3, the device is attached to a source of pressurized fluid, such as an insufflation gas. The gas preferably comprises USP grade carbon dioxide. In other embodiments, the pressurized fluid comprises a liquid such as saline, an isotonic solution, or a non-isotonic solution, which may be delivered, for example, via a gravity bag, fluid pump (e.g. peristaltic pump), or the like. The pressurized insufflation gas may be contained in a vessel or container 310 such as, for instance, a cylinder or tank commonly used in medical applications to store pressurized gases. Alternatively, the pressurized insufflation gas is provided by a hospital or other medical facility that has pressurized gas ports integrated into the construction of individual examination rooms.

The container of pressurized fluid 310 is preferably coupled via a conduit 311 to a shut off valve 312, which can be used to stop all gas flow through the device 100. The shut off valve 312 permits the removal and replacement of the container 310 when it has a low reserve of insufflation fluid. A downstream segment of conduit 311 preferably connects to a pressure regulator 313, which permits the occlusion verification tests described herein to be performed at multitude of pressures or by monitoring the decay of pressure over time. In a preferred embodiment, the pressurized fluid is delivered to the device at a pressure of about 180 to 220 mm Hg, as it is known that a fluid pressure of about 200 mm Hg will open the fallopian tubes of a vast majority of patients. A flow control valve 314 is preferably located downstream of the pressure regulator 313, and serves to control the flow rate of insufflation fluid into the device 100 and therefore the fallopian tube. Also preferably included along the conduit 311 is a valve 315, which operates in either an "off" state or an "on" state.

Figure 4:
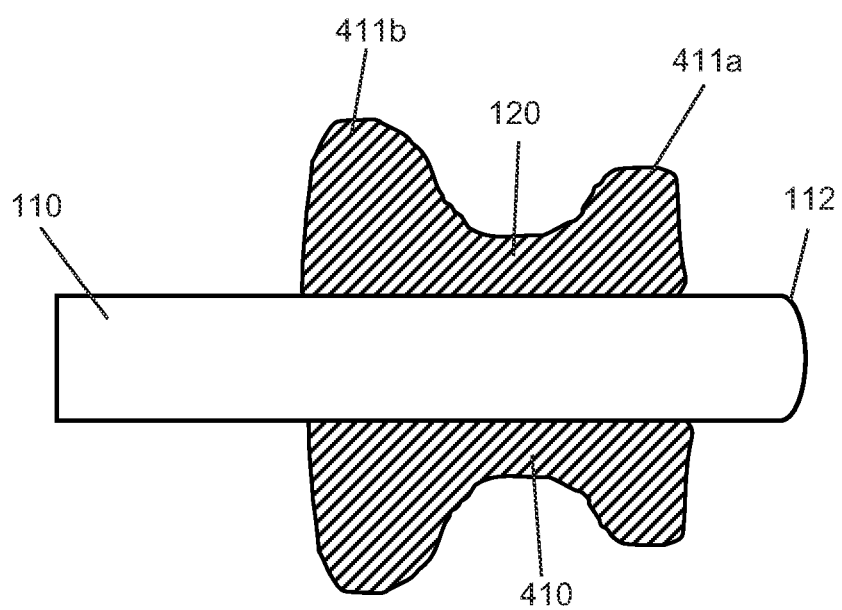
FIG. 4 is a cross-sectional view of a seal member, in accordance with an embodiment of the present invention.

In one embodiment, as shown in FIGS. 1 and 2, the at least one seal member 120 comprises two o-ring shaped features positioned about the elongated body 110 and extending completely around the outer wall 113 of the elongated body 110. Each such o-ring feature provides an independent seal member protruding radially from the outer wall 113 of the elongated body 110. Alternatively, the at least one seal member 120 may comprise a unitary structure 410 extending completely around the outer wall 113 of the elongated body 110 and having a dual-peak profile, as shown in FIG. 4. In this case, each of the peaks 411a and 411b protrude radially from the outer wall 113 of the elongated body 110. In either case, the at least one seal member 120 creates a space 260 bound by the seal member(s) and the patient's tissue when the distal end 112 of the device 100 is inserted to a proper position within the patient's fallopian tube. Because the space 260 is isolated from the fallopian tube and remaining uterus by the at least one seal member 120, the space 260 is intended to remain at a constant pressure, such as atmospheric pressure, during introduction of the pressurized insufflation fluid into the fallopian tube as described herein.

The at least one seal member 120 is made from any suitable material, such as an elastomeric material such as silicone or polyurethane. Alternatively, the at least one seal member 120 is inflatable such as a balloon structure, or comprises a self-expanding structure or material to provide for the necessary seal against surrounding tissue.

The at least one seal member 120 preferably extends a distance of between about 3 mm and about 10 mm from the outer wall 113 of the elongated body 110. When two seal members are used as shown in FIG. 1, it is preferred that, within this 3 mm-10 mm range, the more distal seal member extends a shorter distance from the outer wall 113 than the proximal seal member. This staggered configuration is intended to allow for seal formation when the distal end 112 of the elongated body 110 is inserted into the small diameter fallopian tube 250 such that the more distal seal member is positioned within the fallopian tube, whereas the more proximal seal member is positioned at the less narrow uterotubal junction. The same staggered configuration is the preferred peak configuration when a single seal member is used, as shown in FIG. 4. In other embodiments, seal members extend substantially the same distance from the outer wall 113 of the elongated body 110.

The device 100 includes a first pressure sensor and/or flow meter 130 configured to measure a pressure or fluid flow, respectively, within the continuous open space 116 and the fallopian tube 250 proximal of the implant 300. The first pressure sensor and/or flow meter 130 is preferably a small semiconductor, piezoelectric, capacitive, Micro-Electro-Mechanical (MEMS) based pressure sensor, or semiconductor, ultrasonic Doppler flowmeter, ultrasonic flowmeter, electromagnetic flowmeter, gas microflow sensor, thermoanemometer, or any other suitable electrical, mechanical, or electro-mechanical mechanism for sensing flow and/or pressure. The first pressure sensor and/or flow meter 130 is located in any suitable position within the elongated body, or may be configured to measure the pressure and/or fluid flow within any portion of the conduit 311 or other line that is in fluid communication with the continuous open space 116. In use, a pressurized fluid is preferably delivered into the continuous open space 116, as previously discussed, to a predetermined pressure of preferably about 180-220 mm Hg and then shut off, for example with valve 314, such that the predetermined pressure is maintained. If the fallopian tube 250 is fully occluded, the pressure or fluid flow as measured by the first pressure sensor and/or flow meter 130 should remain substantially constant (i.e., such that the leak down is below a predetermined threshold that accounts for tissue adsorption and the like) over several minutes following the delivery of pressurized fluid into the continuous open space 116 and the fallopian tube 250. If, however, the fallopian tube 250 is not fully occluded, there will be one or more leaks for the passage of the pressurized fluid beyond the implant 300 within the fallopian tube 250. As a result, the pressure as measured by the first pressure sensor will decrease over time, or the fluid flow as measured by the first flow meter (if used) will increase. There will be a certain amount of pressurized fluid that is adsorbed by tissue within the fallopian tube over time such that, even if the fallopian tube is fully occluded, there will be a slight decrease in pressure and/or increase in flow over time. Such change in pressure or flow should be taken into account when determining whether the fallopian tube is fully occluded.

The device 100 includes a second pressure sensor and/or flow meter 140 configured to measure a pressure or fluid flow, respectively, within the space 260 bound by the seal member(s) 120 and the patient's tissue. The second pressure sensor and/or flow meter 140 is preferably a small semiconductor, piezoelectric, or Micro-Electro-Mechanical (MEMS) based pressure sensor. The second pressure sensor and/or flow meter 140 is located in any suitable position on the outer wall 113 the elongated body 110, directly on the seal member(s) 120, or may be configured to measure the pressure and/or fluid flow within any portion of a separate conduit (not shown) that is in fluid communication with the space 260. If the seal member(s) 120 provide an effective seal with surrounding tissue, the second pressure sensor and/or flow meter 140 should measure a substantially constant pressure and/or flow, respectively, throughout the detection process described herein. If, however, the seal member(s) 120 fail to provide an effective seal with surrounding tissue, the pressurized fluid delivered into the fallopian tube 250 will leak into and/or through the space 260 to thereby cause an increase in pressure and/or fluid flow as detected by the second pressure sensor and/or flow meter. As such, the second pressure sensor and/or flow meter 140 provides an indication as to whether any measured change in pressure and/or flow as detected by the first pressure sensor and/or flow meter 130 is attributable to leaks resulting from unsuccessful occlusion of the fallopian tube 250, or rather, to the failure to seal the fallopian tube. Use of the second pressure sensor and/or flow meter 140 thereby addresses the possible limitation of known occlusion verification systems to yield "false positive" results, in which a decrease in insufflation pressure is attributed to a patent fallopian tube although it is actually due to the failure to produce a hermetic seal during the testing procedure. In other embodiments, additional pressure sensors and/or flow meters are used to measure changes in pressure and/or flow. In still other embodiments, a single pressure sensor and/or flow meter is used that measures the pressure and/or flow in two locations such as, for example, by moving it physically or electrically.

The device 100, or at least some distal portion thereof, preferably comprises a flexible material so that it may be deflected into the fallopian tube from a straight cannula 210, as shown in FIG. 2. Preferably, the device 100, or at least some distal portion thereof, is steerable by the use of pull cables or other structures known in the art. In other embodiments, the device 100, or at least some distal portion thereof, is pre-formed into a curved configuration such that when advanced beyond a distal opening of a cannula 210 as shown in FIG. 2, it curves to facilitate introduction into a fallopian tube. In still other embodiments, the device 100 is substantially rigid.

In a preferred embodiment, the device 100 includes a branch line 150 having a distal end 151 and a lumen 152. The lumen 152 opens into the continuous open space 116. In this preferred embodiment, the conduit 311 is connected to the distal end 151 of the branch line 150 to deliver the pressurized insufflation fluid into the elongated body 150, through the distal opening 115 of the elongated body 150, and into a fallopian tube. When the branch line 150 is used, the proximal end 111 of the elongated body 110 may be connected to a separate line for the exhaust of the pressurized fluid following the detection or verification of tubal occlusion, or it may be connected to the first pressure sensor and/or flow meter 130 when detached from the elongated body 110, or it may be capped during the test procedure.

The device 100 optionally includes or works in conjunction with a visual and/or audible alarm. The alarm is adapted to be triggered upon either of a pressure or flow change as measured by the first pressure sensor 130 to signal that the fallopian tube 250 is not fully occluded, or a pressure or flow change as measured by the second pressure sensor 140 to signal that a seal has not been properly made with the fallopian tube 250 during the test procedure.

The device 100 optionally includes means for detecting contact between the at least one seal member 120 and surrounding body tissue. For example, the device may include one or more electrical contacts on the at least one seal member 120. Shorting these contacts by contact with tissue provides an indication that the at least one seal member 120 is in contact with surrounding tissue, thus suggesting that the at least one seal member 120 will provide a hermetic seal with surrounding tissue during use of the device 100. As another example, the at least one seal member 120 may include small openings through which a negative pressure, or vacuum, is applied. The negative pressure will pull the at least one seal member 120 against the surrounding tissue. A decrease in pressure within the vacuum line would provide an indication that the at least one seal member 120 is contact with surrounding tissue, thus suggesting that the at least one seal member 120 will provide a hermetic seal with surrounding tissue during use of the device 100.

Figure 5:
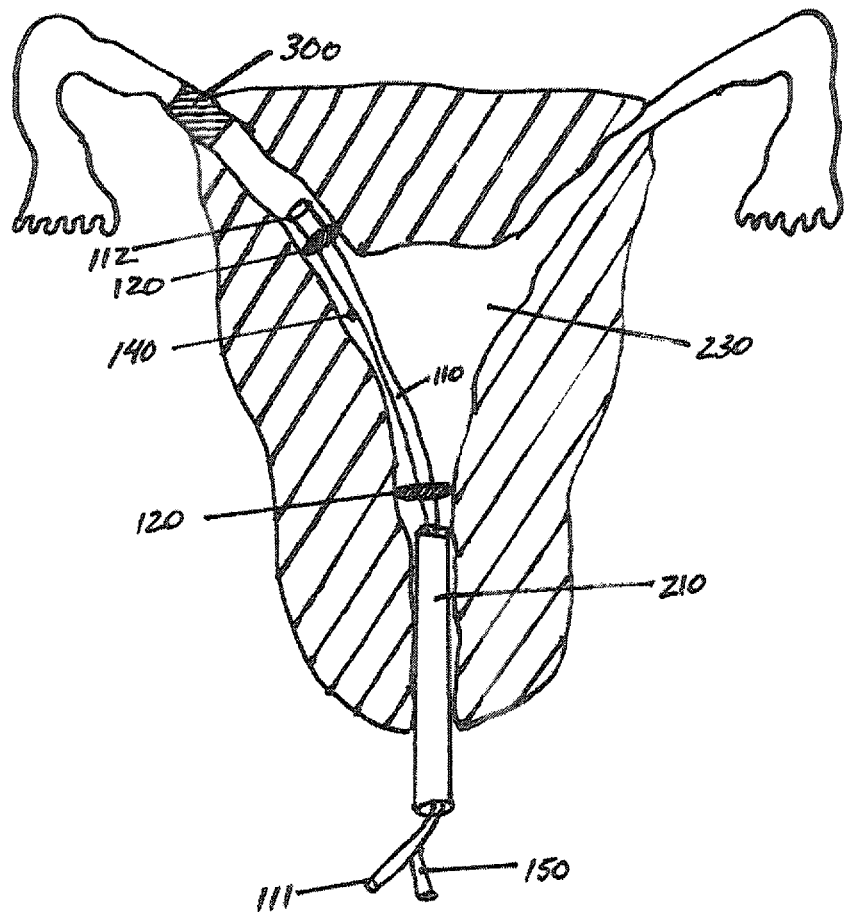
FIG. 5 illustrates the placement of a device of the present invention into the fallopian tube of a patient, in accordance with an embodiment of the present invention.

In an alternate embodiment as shown in FIG. 5, the device 100 includes two seal members 120 with one of the seal members being positioned along the elongated body 110 such that it forms a seal at or near the cervical os (internal or external) rather than at the uterotubal junction. In contrast to the embodiment shown in FIG. 2, the second pressure sensor and/or flow meter 140 in the embodiment shown in FIG. 5 is configured to measure the pressure and/or flow within a large portion of the uterus 230 during the test procedure of the present invention.

The present invention provides for the detection and verification of lumen occlusion with advantages not previously known. Although the present invention is described with specific reference to the detection and verification of fallopian tube occlusion for sterilization purposes, it is intended that the present invention be applicable to the detection and verification of lumen occlusion within any bodily lumen or space, such as the vas deferens, blood vessels, and bodily lumens within the GI tract or urinary tract. Furthermore, it will be apparent to those skilled in the art that various modifications and variations can be made in the structure and methodology of the present invention. It is intended that the present invention cover the modifications and variations of this invention provided that they come within the scope of the appended claims and their equivalents.

What is claimed is:

1. A method for determining fallopian tube occlusion using a pressure sensing probe, the probe comprising an elongate probe body having a sealing member disposed on, and protruding radially from, an outer surface of the probe body, the method comprising:

positioning a distal portion of the probe body in a fallopian tube, thereby isolating an interior volume of the fallopian tube bounded in part by the sealing member and the inner wall of the fallopian tube, wherein the sealing member comprises first and second annular seal members that define an annular space between the annular seal members and the interior wall of the fallopian tube when the distal portion of the probe is positioned within the fallopian tube;

administering a pressurized fluid into the isolated interior volume of the fallopian tube through a distal opening of the probe body located distally of the sealing member;

monitoring a pressure of the isolated interior volume of the fallopian tube to determine whether the fallopian tube is occluded; and monitoring a seal formed between the sealing member and the inner wall of the fallopian tube to determine whether a pressure-tight seal is maintained by the sealing member while monitoring the pressure of the isolated interior volume of the fallopian tube, in order to verify that a decrease in pressure of the isolated interior volume of the fallopian tube is due to non-occlusion of the fallopian tube, wherein monitoring the seal formed between the sealing member and the inner wall of the fallopian tube comprises monitoring a pressure of the annular space.

2. The method of claim 1, wherein one or both of the first and second annular seal members are inflatable.

3. The method of claim 1, wherein the first and second annular seal members extend between about 3 mm and about 10 mm from the outer surface of the probe body.

4. The method of claim 1, further comprising detecting tissue contact by the sealing member.

5. The method of claim 1, wherein the fluid is administered to the isolated interior volume of the fallopian tube at a pressure within the range of 180 to 220 mm Hg.

6. The method of claim 1, wherein the fluid is a gas.

7. The method of claim 1, the probe body further having a proximal opening and a lumen that fluidly couples the proximal and distal openings, and wherein the pressure of the isolated interior region of the fallopian tube is monitored using a sensor located within the lumen.

8. The method of claim 1, wherein the pressure of the annular space is monitored using a sensor located within the annular space.

9. A method for determining fallopian tube occlusion using an occlusion detecting probe, the probe comprising an elongate probe body having a sealing member disposed on, and protruding radially from, an outer surface of the probe body, the method comprising:

positioning a distal portion of the probe body in a fallopian tube thereby isolating an interior volume of the fallopian tube bounded in part by the sealing member and the inner wall of the fallopian tube, wherein the sealing member comprises first and second annular seal members that define an annular space between the annular seal members and the interior wall of the fallopian tube when the distal portion of the probe is positioned within the fallopian tube;

administering a pressurized fluid into the isolated interior volume of the fallopian tube through a distal opening of the probe body located distally of the sealing member;

monitoring a flow rate of the administered pressurized fluid to determine whether the fallopian tube is occluded; and monitoring a seal formed between the sealing member and the inner wall of the fallopian tube to determine whether a fluid-tight seal is maintained by the sealing member while monitoring the flow rate of the administered pressurized fluid, in order to verify that a reduction in the flow rate of the administered pressurized fluid below a predetermined threshold is due to non-occlusion of the fallopian tube, wherein monitoring the seal formed between the sealing member and the inner wall of the fallopian tube comprises monitoring fluid flow into the annular space.

10. The method of claim 9, wherein one or both of the first and second annular seal members are inflatable.

11. The method of claim 9, wherein the first and second annular seal members extend between about 3 mm and about 10 mm from the outer surface of the probe body.

12. The method of claim 9, further comprising detecting tissue contact by the sealing member.

13. The method of claim 9, the probe body further having a proximal opening and a lumen that fluidly couples the proximal and distal openings, and wherein the flow rate of the administered pressurized fluid is monitored using a sensor located within the lumen.

14. The method of claim 9, wherein the fluid flow within the annular space is monitored using a sensor located within the annular space.

15. A method for determining fallopian tube occlusion using an occlusion detection probe, the probe comprising an elongate probe body having a sealing member disposed on, and protruding radially from, an outer surface of the probe body, the method comprising:

positioning a distal portion of the probe body proximate a fallopian tube such that the sealing member isolates an interior volume of the fallopian tube bounded in part by sealing member and an inner wall of the fallopian tube, the sealing member comprising first and second annular seal members defining an annular space between the annular seal members and the interior wall of the fallopian tube when the distal portion of the probe is positioned within the fallopian tube;

administering a pressurized fluid into the isolated interior volume of the fallopian tube through a distal opening of the probe body located distally of the sealing member;

monitoring one of a pressure or flow rate of the pressurized fluid in the isolated interior volume of the fallopian tube to determine whether the fallopian tube is occluded; and monitoring one of a pressure of, or a flow rate within, the annular space defined by the first and second sealing members to determine whether a fluid-tight seal is maintained by the sealing member while monitoring the pressure or flow rate of the pressurized fluid introduced into the isolated interior volume of the fallopian tube.

16. The method of claim 15, wherein the pressure of, or flow rate within, the annular space is monitored using a sensor located within the annular space.

* * * * *